(12) United States Patent
Borth et al.

(10) Patent No.: US 8,026,822 B2
(45) Date of Patent: Sep. 27, 2011

(54) NETWORKED PEST CONTROL SYSTEM

(75) Inventors: Paul W. Borth, Zionsville, IN (US);
Peter N. Scherer, Lebanon, IN (US);
Mike P. Tolley, Indianapolis, IN (US);
Christopher J. Voglewede, Lafayette, IN (US); Brian M. Schneider, Carmel, IN (US); Nailah Orr, Carmel, IN (US); Richard V. Baxter, Jr., Appleton, WI (US); Douglas K. Brune, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 106 days.

(21) Appl. No.: 12/584,581

(22) Filed: Sep. 8, 2009

(65) Prior Publication Data

US 2010/0134301 A1    Jun. 3, 2010

Related U.S. Application Data

(60) Provisional application No. 61/191,461, filed on Sep. 9, 2008.

(51) Int. Cl.
*G08B 23/00* (2006.01)
(52) U.S. Cl. .................................. 340/573.2; 340/573.1
(58) Field of Classification Search ............... 340/573.2, 340/573.1, 531; 73/865.8; 43/82, 132.1
See application file for complete search history.

(56) References Cited

U.S. PATENT DOCUMENTS

| 7,212,129 B2 | 5/2007 | Barber et al. |
| 7,348,890 B2 | 3/2008 | Barber et al. |
| 2003/0151513 A1* | 8/2003 | Herrmann et al. ......... 340/573.1 |
| 2006/0176169 A1 | 8/2006 | Doolin et al. |
| 2007/0192032 A1 | 8/2007 | David et al. |
| 2008/0204253 A1* | 8/2008 | Cottee et al. ............... 340/573.2 |

FOREIGN PATENT DOCUMENTS

| WO | WO 03/061175 A2 | 7/2003 |
| WO | WO 2004/021735 A1 | 3/2004 |
| WO | WO 2006/101654 A2 | 9/2006 |
| WO | WO 2007/026123 A1 | 3/2007 |

OTHER PUBLICATIONS

Notification of Transmittal of International Preliminary Report on Patentability; PCT/US09/05056.

* cited by examiner

*Primary Examiner* — John A Tweel, Jr.
(74) *Attorney, Agent, or Firm* — Carl D. Corvin; Krieg Devault LLP

(57) ABSTRACT

A pest control device system includes a plurality of pest control devices and a data collector. The system may further include the data collector in the form of a gateway that is connected to a data management server via a computer network along with other gateways in corresponding pest control device groups. Each pest control device includes a pest sensor and a wireless communication circuit to transmit information from the corresponding sensor. The devices also configure to define a local wireless communication network that can relay the information from one to the next and ultimately to the data collector.

22 Claims, 6 Drawing Sheets

NETWORKED PEST CONTROL SYSTEM

CROSS-REFERENCE TO RELATED APPLICATIONS

The present application claims the benefit of U.S. Provisional Patent Application No. 61/191,461 filed on 9 Sep. 2008, which is hereby incorporated by reference in its entirety.

BACKGROUND

The present invention relates to pest control, and more particularly, but not exclusively, relates to techniques for sensing, communicating, storing, and evaluating data from networked pest control devices.

The detection and removal of pests from areas occupied by humans, livestock, crops, and other pest-attracting areas has long been a challenge. Pests of frequent concern include various types of insects and rodents. Subterranean termites are a particularly troublesome type of pest with the potential to cause severe damage to wooden structures. Likewise, other insects, such as bedbugs, are problematic. Additionally, rodent control is often challenging. Various schemes have been proposed to eliminate these and certain other harmful pests.

Recently, advances have been made to provide for the targeted delivery of pesticide chemicals only after pests have been detected. One example is the SENTRICON TERMITE COLONY ELIMINATION SYSTEM™ of Dow AgroSciences that has a business address of 9330 Zionsville Road, Indianapolis, Ind. In this system, a number of stations are installed in the ground about a dwelling to be protected. A pest control service provider periodically checks the stations, which can be labor-intensive.

Similarly, rodent traps in food processing/storage facilities, pharmaceutical production facilities, and the like need to be routinely checked—resulting in significant labor expenditures. Accordingly, there is a demand for alternative pest control device monitoring techniques. Alternatively or additionally, the ability to gather more comprehensive data relating to pest behavior is sought. Thus, there is a continuing demand for further advancement in the area of pest control and related sensing technologies.

SUMMARY

One embodiment of the present invention includes a unique pest control and/or monitoring technique. Other embodiments include unique methods, devices, and systems to control pests and/or monitor pest activity. Further embodiments, forms, objects, features, advantages, aspects, and benefits shall become apparent from the following description and drawings.

DETAILED DESCRIPTION OF REPRESENTATIVE EMBODIMENTS

Figure 1:
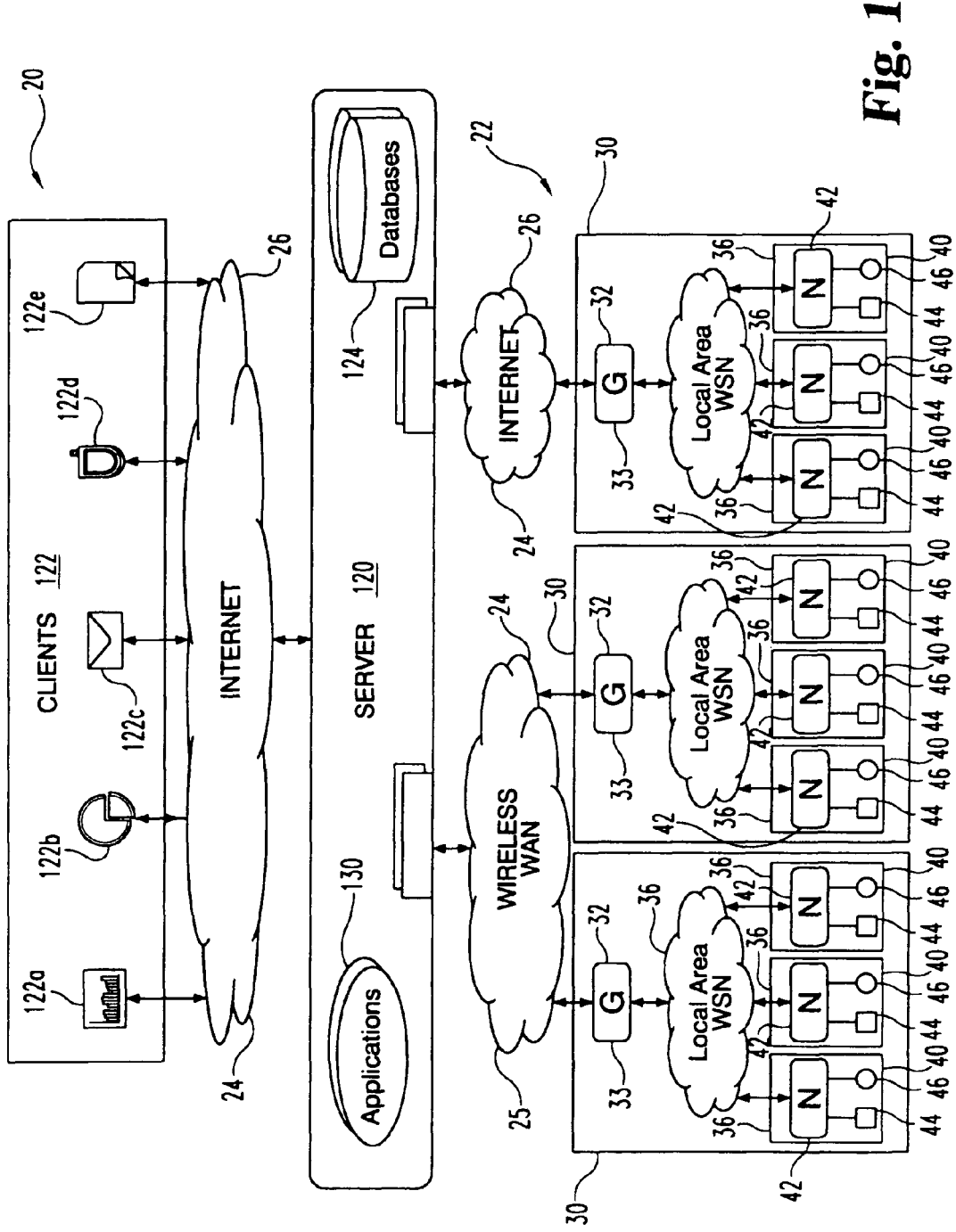
FIG. 1 is a diagrammatic view of a pest control system that includes several pest control devices.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present application is a system that includes a data collection point and several spaced-apart pest control devices. The pest control devices each include a sensor and wireless communication circuitry. At least some of the pest control devices are structured to relay information received from one or more other of the pest control devices to the data collection point. In one form, the data collection point is in communication with a remotely located data management server via a computer network. Alternatively or additionally, the data collection point can be a form of gateway structured to collect information from each control device and communicate it to a remote destination.

FIG. 1 depicts pest control system 20 of the present application. System 20 includes a pest control monitoring arrangement 22 that communicates with a central pest data management server 120 by computer network 24. Computer network 24 is more specifically depicted in two nonlimiting forms as a wireless Wide Area Network (WAN) 25 and internet 26 in FIG. 1. A number of clients 122 of server 120 are also depicted that can selectively access server 120 through internet 26. Client 122 includes browser subsystem 122a, spreadsheet interface 122b, email interface 122c, Short Message Service (SMS) interface 122d, and other interface subsystems 122e. It should be appreciated that while wireless WAN 25 and internet 26 are specifically depicted, other types of data communication networks can be utilized additionally or alternatively.

Pest control monitoring arrangement 22 includes a number of pest control device groups 30 that each may be installed at a different location to monitor/control one or more types of pests of interest. Each pest control device group 30 includes a pest control data collector 32 in a communication gateway 33, and several pest control devices 40. Gateway 33 interfaces with server 120 via computer network 24 and interfaces with pest control devices 40 via wireless Local Area Network (LAN) 36. Devices 40 each include a communication node 42 that collectively define network 36. Each device 40 includes bait 44 in the form of a pest-consumable material, lure, attractant, or the like; however, in other embodiments, an attractant, lure or other form of bait may be absent. The depicted embodiment of device 40 further includes pest sensor 46.

For a given pest control device group 30, pest control devices 40 may be arranged to monitor/protect a designated building, room, storage area, or region from a pest of concern, such as rodents, termites, bedbugs, other troublesome insects, and various pests attracted to stored grain, animal feed, pharmaceuticals, pharmaceutical components, other biologic materials, or the like. Accordingly, bait 44 and sensor 46 are selected relative to the pest type(s) of interest. Nonlimiting examples of various sensor and bait types for pest control devices are described in commonly owned U.S. Pat. Nos.

7,348,890; 7,262,702; 7,212,129; 7,212,112; 6,914,529; and 6,724,312, each of which is hereby incorporated by reference in its entirety. These patents also describe the manner in which different areas are monitored by devices employing such sensors, among other things.

Figure 2:
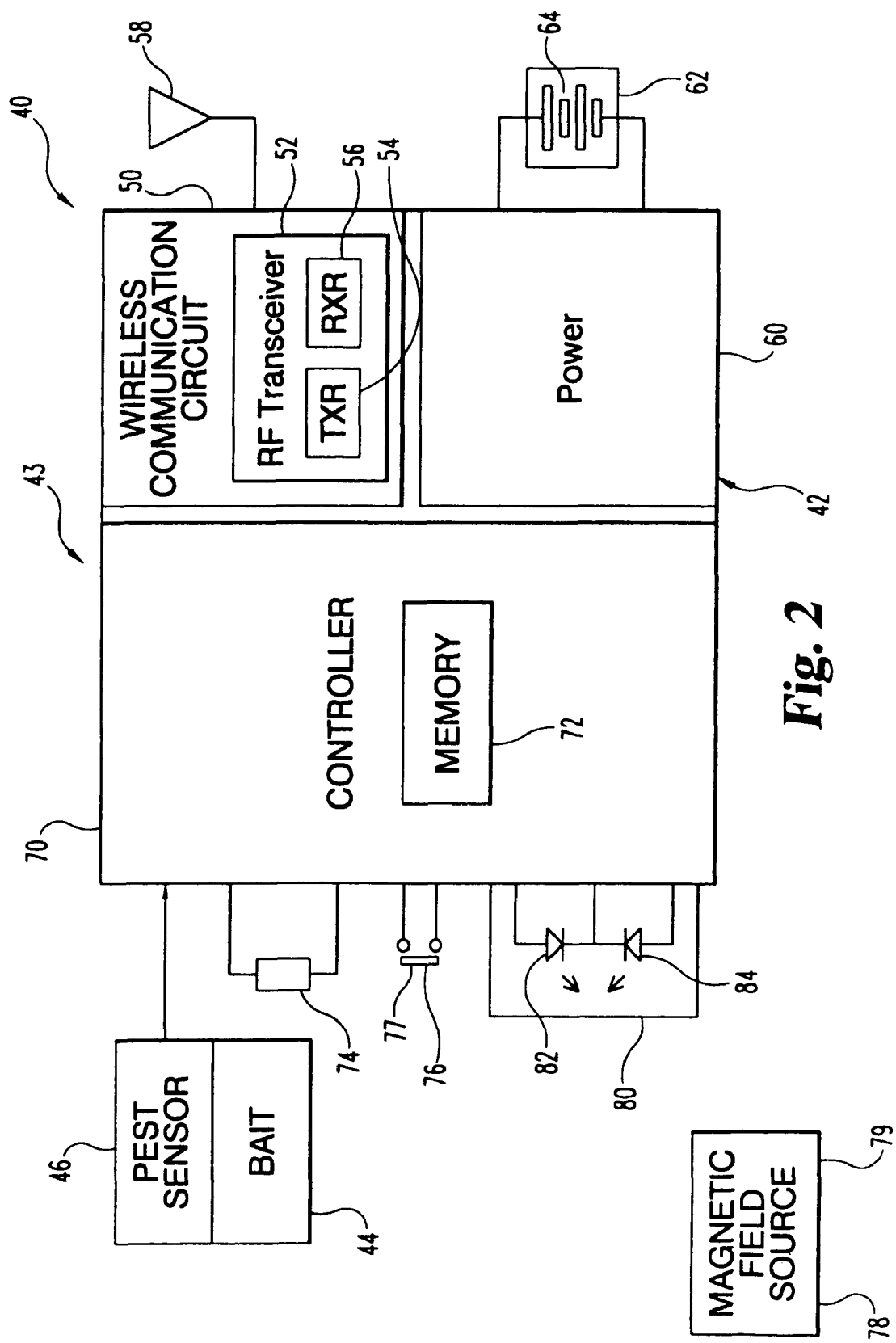
FIG. 2 is a diagrammatic view of a pest control device that can be included in the system of FIG. 1.

FIG. 2 shows pest control device 40 in greater detail; where like reference numerals refer to like features previously described. Pest control device 40 includes electrical circuitry 43. Circuitry 43 includes wireless communication circuitry 50 that defines wireless communication node 42. Specifically, circuitry 50 includes RF transceiver 52 that in turn includes transmitter (TXR) 54 and receiver (RXR) 56. Circuit 50 further includes communication antenna 58. It should be appreciated that at least a portion of transmitter 54 and receiver 56 can be provided in the same integral unit. For example, commonly shared aspects would include antenna 58 and/or RF front-end circuitry; however, in other arrangements transceiver 52 is defined by independent transmitter 54 and receiver 56 units that collectively provide both transmission and reception functionality.

Node 42 further includes power management circuitry 60 and controller 70. Circuitry 60 includes electrical power source 62 in the form of one or more electrochemical cells or battery 64. Circuitry 60 conditions and provides electrical power to node 42 and sensor 46 as needed.

Controller 70 includes memory 72. Controller 70 can be an electronic circuit comprised of one or more components, including digital circuitry, analog circuitry, or both. Controller 70 may be a software and/or firmware programmable type; a hardwired, dedicated state machine; or a combination of these. In one embodiment, controller 70 is a programmable microcontroller solid-state integrated circuit that integrally includes a processing unit and memory 72. Nonlimiting examples include model nos. MSP430F147 and MSP430F149 provided by Texas Instruments Incorporated. Memory 72 can be comprised of one or more components and can be of any volatile or nonvolatile type, including the solid state variety, the optical media variety, the magnetic variety, a combination of these, or such different arrangement as would occur to those skilled in the art. Further, more than one processing unit can be included. When multiple processing units are present, controller 70 can be arranged to distribute processing among such units, and/or to provide for parallel or pipelined processing if desired. Controller 70 functions in accordance with operating logic defined by software and/or firmware programming, hardware, or a combination of these. In one form, memory 72 stores program instructions that are executed by one or more processing units of controller 70 to embody at least a portion of this operating logic. Alternatively or additionally, memory 72 stores data that is manipulated by the operating logic of controller 70. Controller 70 can include signal conditioners, signal format converters (such as analog-to-digital and digital-to-analog converters), limiters, clamps, filters, dedicated timers, and the like as needed to perform various operations described in the present application. Indeed, in one form, controller 70, wireless communication circuitry 50 and power management circuitry 60 are at least partially defined by the same integrated circuit device.

Pest sensor 46 is electrically coupled to controller 70 to provide a corresponding signal indicative of pest presence and/or activity. In one form, sensor 46 provides an electrical input to an analog-to-digital converter (ADC) included in controller 70. Pest sensor 46 is associated with bait 44 that may be of a food or other material commonly consumed by pests of interest and/or a lure, attractant, or the like. It should be appreciated that as used herein, bait 44 may or may not include a pesticide and may or may not be intended to be more attractive to pests of interest compared to other materials in proximity. In one arrangement, pest interaction with bait 44 triggers a change in the signal sent by sensor 46. Typically, detection is triggered by a variation in electrical current or voltage. In one form, such variation results from a change in electrical conductivity/resistance of one or more elements of sensor 46 in correspondence to pest presence. Alternatively or additionally, a detection signal could be generated based on electrical capacitance, magnetism, an acoustic characteristic, or optical change—just to name a few alternatives. Commonly owned U.S. Pat. Nos. 7,348,890; 7,262,702; 7,212,129; 7,212,112; 6,914,529; and 6,724,312, describe several such sensing techniques (which were previously each incorporated by reference). It should be appreciated that while one pest sensor 46 is indicated in FIG. 2, in other arrangements multiple pest sensors may be utilized with inputs provided to controller 70 and/or a different device. Furthermore, in other alternative arrangements, bait 44 may be absent.

In one implementation, pest control devices 40 are configured to operate with a standard battery power source for at least two years, communicating only a relative small amount of data routinely (such as an average of six times per day), with a transmission distance minimum of about 10 meters under very poor conditions and greater than 100 meters under favorable conditions. Nonetheless, in other arrangements any or all of these aspects could vary. In typical termite applications, pest control device 40 takes the form of an in-ground station with an electrically conductive pathway that is altered by termite consumption or displacement to trigger detection. With this arrangement, pesticide may not be delivered until termite presence is verified, although immediate pesticide application and/or above-ground monitoring may be utilized additionally or alternatively. Some rodent applications tend to favor extermination upon detection using a pesticide, mechanical force, and/or electrocution.

Figure 3:
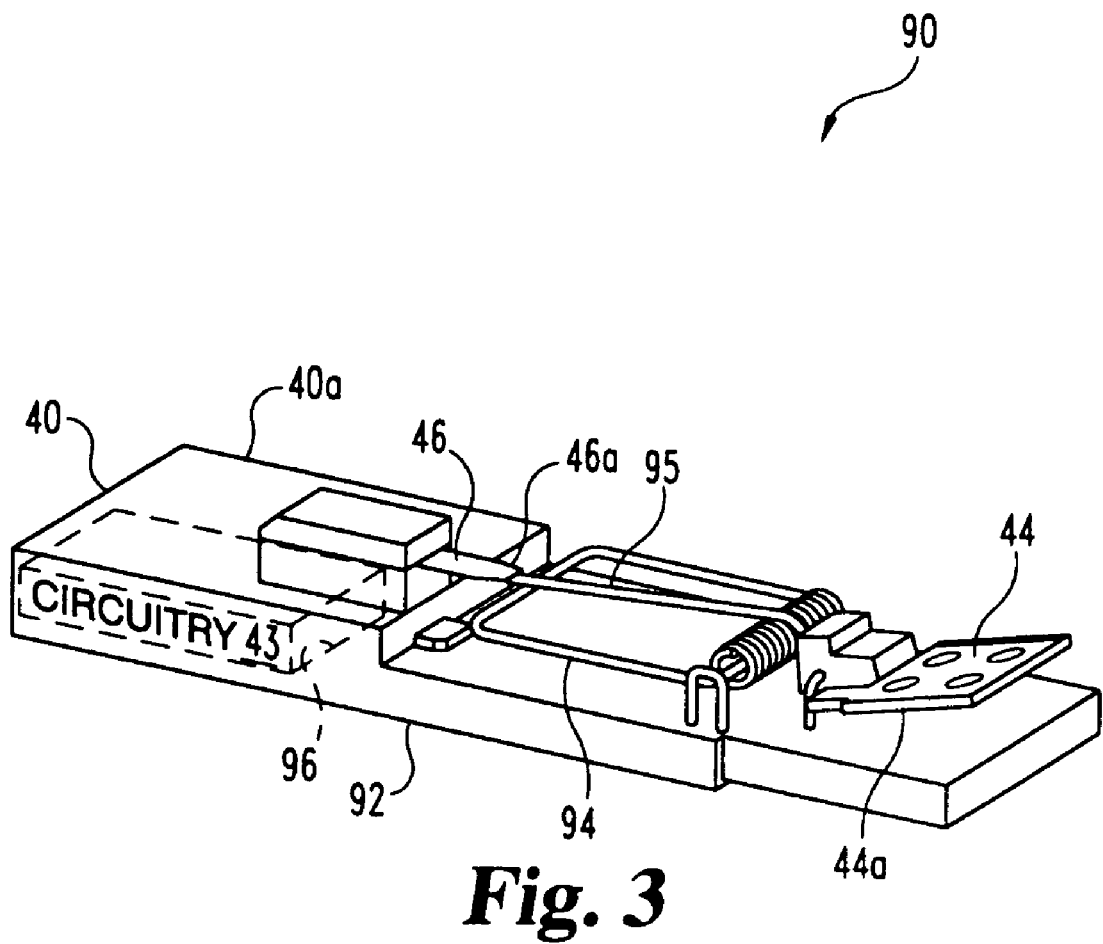
FIG. 3 is a perspective view of one form of a rodent control device that can be included in the system of FIG. 1.

In one example, FIG. 3 a form of pest control device that integrates sensor 46 with snap-type of rodent trap 90; where like reference numerals refer to like features previously described. In this arrangement, sensor 46 more specifically includes a flexible detection member 46a with an electrical resistance that varies depending on the degree of its mechanical deflection/flexure. Trap 90 includes a base housing 92 that is pivotally coupled to spring 94. Spring 94 is held in place by trap pin 95 as shown in FIG. 3. In this configuration, if a rodent applies sufficient downward pressure on bait plate 44a, pin 95 is displaced and spring 94 is released to pen the rodent between the spring 94 and base housing 92. Correspondingly, the deflection of member 46a changes in response to the displacement of pin 95, causing a change in its electrical resistance. Member 46a is electrically coupled to circuitry 43 to provide a corresponding signal indicative of the triggering of the trap and rodent detection. Circuitry 43 resides in chamber 96 defined by base housing 92. Alternatively or additionally, rodent and/or other pest control devices may include a pressure-sensitive pad to detect presence. Further, it should be appreciated that while pest presence is typically the detection goal, any activity/actuation of sensor 46 may be of interest for a given pest control scheme.

Returning to FIG. 2, circuitry 43 further includes temperature sensor 74 coupled to controller 70, which, without limitation could be a thermistor, a thermocouple, or the like that provides an analog input to an ADC unit within controller 70. In other embodiments, a moisture sensor may be included in addition to or in lieu of temperature sensor 74. In still other embodiments neither of these sensor types is present. Also included in circuitry 43 is an operator-activated switch 76 of a magnetic form comprised of a magnetically-responsive component 77 (such as a hall-effect device or magnetoresistor to name a couple of nonlimiting examples) and an indicator 80, both of which are also coupled to controller 70. Switch 76 is arranged to respond to a magnetic field when magnetic field source 78 is in close proximity thereto. In one form, magnetic field source 78 is provided in the form of a hand-held wand 79. Indicator 80 includes two Light Emitting Diodes (LEDs) 82 and 84 each of a different color. In one particular nonlimiting example, one of LEDs 82 and 84 is red, while the other of LEDs 82 and 84 is green. The operation of these features is further described hereinafter in connection with FIG. 4; however, further aspects to gateway 33 are first described in connection with FIG. 5. In other embodiments, switch 76 may be of a mechanical variety, such as a pushbutton, rotary, slider, or toggle type; a capacitive proximity type, an optic type, or a thermally activated type—just to name a few possibilities. In one nonlimiting alternative, rodent trap activation was demonstrated with a pushbutton form of switch.

Figure 5:
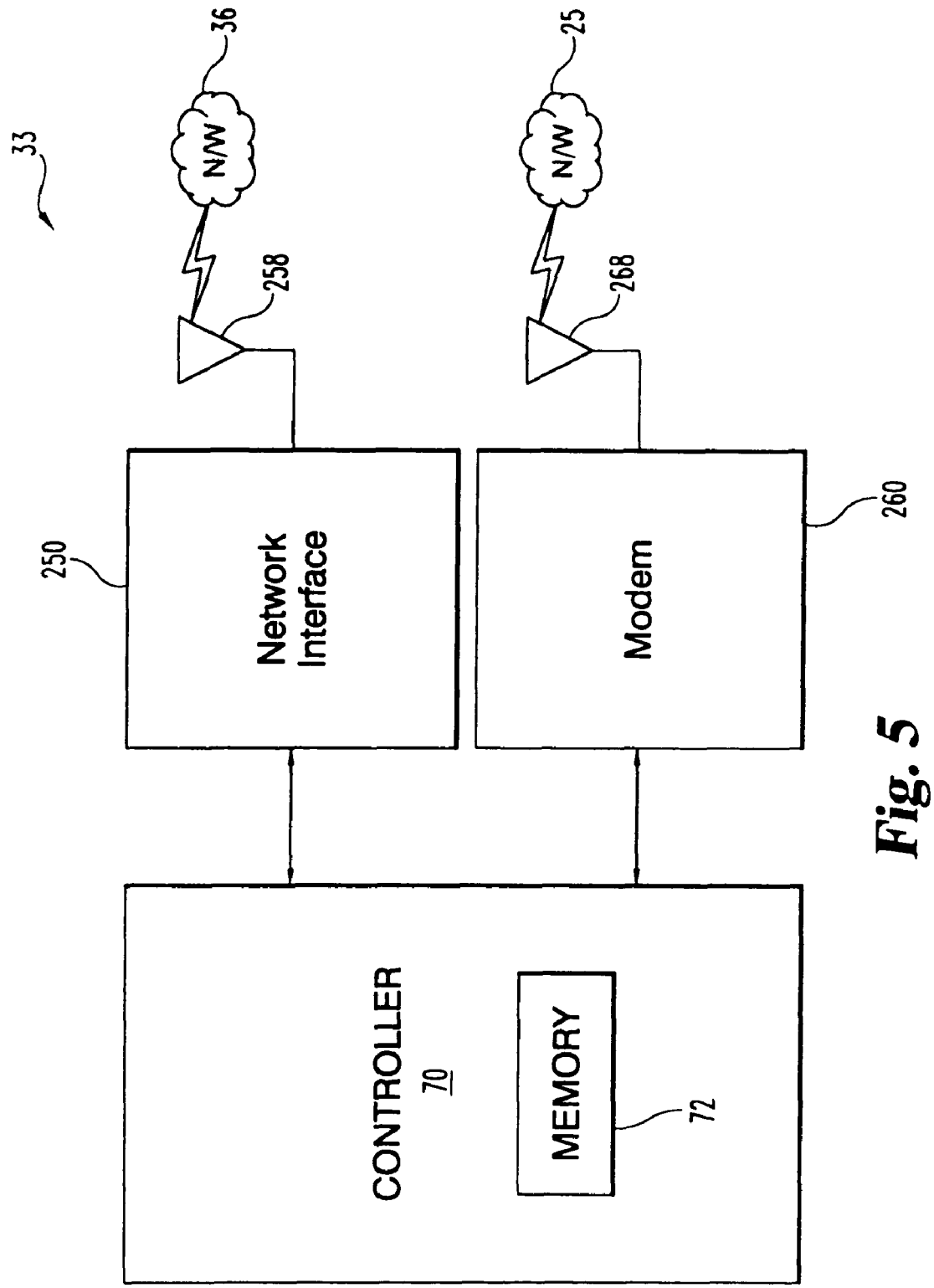
FIG. 5 is a diagrammatic view of a gateway of the system of FIG. 1.

Referring to FIG. 5, gateway 33 is further depicted; where like reference numerals refer to like features previously described. Gateway 33 includes controller 70 with memory 72. Gateway 33 further includes a wireless network interface 250 with antenna 258 to communicate with the wireless communication network 36, as defined by a corresponding pest control group 30; and modem 260 with antenna 268 to interface with a wireless WAN network 25. In one nonlimiting form, controller 70 is a general purpose laptop or personal computer running an application to define a communication gateway, interface 250 is of a local area network (LAN) type, and modem 260 utilizes General Packet Radio Service (GPRS) through the Global System for Mobile communications (GSM) protocol. It should be appreciated that in alternative embodiments, controller 70, interface 250, and/or modem 260 may differ. In one such alternative in which gateway 33 directly interfaces with internet 26, controller 70 is of a microcontroller type, such as model no. C805F120 provided by Cygnal Technologies; interface 250 is a 25 milliWatt (mW) WAVENIS-compatible wavecard provided by Coronis Systems; and modem 260 is of a hardwired dial-up and/or coaxial cable type (not shown).

Figure 4:
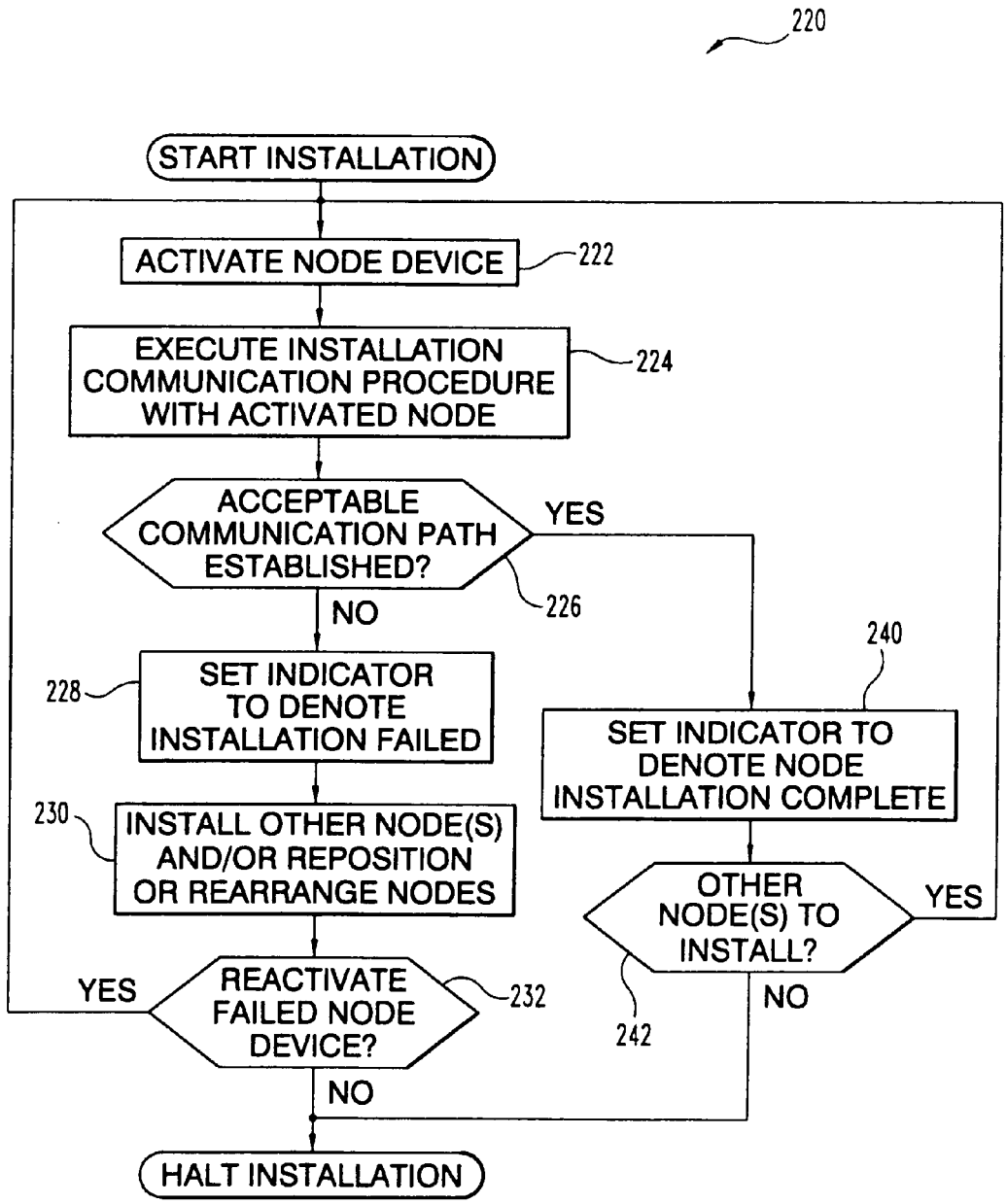
FIG. 4 is a flowchart depicting one procedure for installing the pest control devices of the system of FIG. 1.

Having generally described the structural and functional aspects of group 30, further details regarding its operation are next described. Initially, pest control devices 40 of a respective group 30 are installed to protect the building/area of interest, which includes physically positioning each of pest control devices 40 and establishing wireless network 36. FIG. 4 depicts one mode of establishing network 36 in flowchart form as network installation procedure 220; where like reference numerals refer to like features previously described. Procedure 220 can be implemented in accordance with operating logic executed by controller 70 of at least some of the pest control devices 40 and gateway 33 for the respective group 30. Procedure 220 logically associates each node 42 with a corresponding gateway 33. During procedure 220, each node 42 attempts to establish a reliable communications path to the respective gateway 33, either directly or by relaying its messages through one or more other nodes 42 of the same group 30, and provides the installer feedback concerning its success or failure in finding a reliable communications path. Specifically, in operation 222, a selected node 42 is activated. For the magnetically-responsive component 77 form of switch 76, a magnetic field from source 78 is placed in close proximity. In response, switch 76 changes state and triggers network establishment for such selected node 42. In an alternative implementation, an operator triggers node network installation activation by applying force to a mechanical form of switch 76, such as pushing a momentary, pushbutton switch type.

In response to node activation in operation 222, procedure 220 continues with operation 224. In operation 224, the selected node 42 executes a search routine to identify a reliable communication path to its corresponding gateway 33. This routine is typically defined by operating logic executed by controller 70 of the selected node. In one implementation, this routine is at least partially provided in the form of firmware instructions stored in memory 72 and uses a SEARCH REQUEST function included in the Service Discovery Protocol (SDP) code library. This function can operate with a variety of criteria for the requested search, including a Class of Device (COD) code identifying the specific gateway 33 to which connection is desired, quality of service (QoS) criteria based on signal strength or the like, and criteria controlling the preferred method of making the connection, either directly to gateway 33 or through one or more other nodes 42 of its pest control device group 30. As establishment of a communication pathway is attempted, indicator 80 provides an output reflecting this status. In one form, this output includes LEDs 82 and 84 both blinking at approximately a 10 Hertz (Hz) rate; however, other outputs and/or no output may be provided in correspondence to operation 224 in other embodiments.

Operation 224 first attempts to find a direct communications path with the corresponding gateway 33 provided it meets specified quality of service (QoS) criteria—such as signal strength. If a direct path meeting the search criteria is not found, then operation 224 attempts to find a communications path to gateway 33 through other nearby nodes 42 that have already gone through the network installation procedure 220 (if any). The criteria for these "indirect" communication paths can be different than those for direct connections, and take into account, in addition to signal strength, how many "hops" are required and/or how many other devices might already be routed through a given node 42 operating as a repeater. In some implementations, a limit may be set on the number of communication hops required to reach the corresponding gateway 33, a limit may be set on the number of relaying/repeating nodes 42 involved in a given communication pathway, and/or a limit may be set on how may nodes 42 depend on a specific node 42 to relay communication.

Procedure 220 continues with conditional 226 that tests whether the desired communication path has been established. If the test of conditional 226 is affirmative (yes), data designating the communication path is stored and a success code is returned—reflecting that a direct or indirect path meeting the search criteria has been found. Further, using the identified communication path, the selected node 42 communicates a unique identifier (such as a unique multibit identification code) to its corresponding gateway 33 of the same group 30. Procedure 220 continues with operation 240 to provide an output indicating success with indicator 80. In one form, this output includes illuminating one of LEDs 82 or 84, such as a green LED, for a specified period of time (such as 10 seconds, for example). From operation 240, procedure 220 continues with conditional 242 to determine if there are any more nodes 42 to install. If not, then procedure 220 halts. If there are further nodes to install, procedure 220 returns to operation 222 to select and activate the next node 42 for network installation.

On the other hand, if all attempts to find a communications path meeting the criteria are not successful, operation 224 returns a failure code, and the test of conditional 226 is negative (no). From the negative branch of conditional 226, operation 228 is performed in which indicator 80 provides an operator output reflecting this negative/failure status. In one form, this output includes illuminating one of LEDs 82 or 84 different than for operation 240, such as a red LED, for a specified period of time (such as 10 seconds, for example).

Procedure 220 proceeds from operation 228 to operation 230. In operation 230, the operator installs one or more other nodes 42 to serve as repeaters and/or repositions the selected node 42 to provide better conditions for network establishment. It should be appreciated that the successful installation of any other node 42 during operation 230 includes the repetition of operations 222, 224, and 240 and conditionals 226 and 242 for each, and likewise, any that were not successful would result in execution of operations/conditional 222-230. After operation 230, conditional 232 is reached. Conditional 232 tests whether the node 42 that failed initialization should be reactivated for another attempt. Ordinarily, this test would be affirmative (yes), causing procedure 220 to return to operation 222 to reactivate it; however, under certain circumstances it may be determined to abort installation of a given node 42. Such circumstances may include several failed attempts to install or the successful installation of the desired number and/or arrangement of nodes 42 already, such that the failed node 42 need not be installed. In this case, the test of conditional 232 is negative (no) and procedure 220 halts.

Once network 36 is established, each pest control device 40 and gateway 32 perform certain operations on a routine basis. In one embodiment, each node 42 participating in network 36 has a low-power consumption sleep mode and at least one "awake" mode. For one form, the sleep mode is performed based on an internal sleep timer provided by controller 70, that allows the node 42 to significantly reduce its power consumption during idle periods and accordingly enables longer service life. For such a sleep mode, the transceiver 52 and/or other peripherals are typically turned off to conserve power.

After a designated time period has passed during sleep mode, a wake-up is triggered. In one form, a sleep timer is programmed to wake-up controller 70 every 100 milliseconds (10 times per second), and the operating logic, as defined at least in part by controller firmware, is divided into time-based tasks, some of which are executed every wakeup period (100 milliseconds) and others that are executed every tenth wakeup (1 second).

For this arrangement, the 100 millisecond tasks include sensor signal measurements and evaluation of such signals for possible action. In one particular variation, node 42 includes an internal, multi-channel 12-bit A/D converter for measuring analog signals from external sources over three different channels. One channel is used for pest sensor 46 input, a second channel is used for temperature sensor 74 input, and a third channel is connected to battery 64 to report on its status. The resulting digital values are stored in memory 72 and are compared against designated limits for LOW FAULT, LOW ALARM, LOW WARNING, HIGH WARNING, HIGH ALARM, and HIGH FAULT conditions. If any FAULT, WARNING, or ALARM condition is detected, an event message is provided for transmission to gateway 33 indicating the affected channel/source, condition (FAULT, WARNING, or ALARM), and the measured value. Any or all of these condition tests may be optionally disabled. Hysterisis can be applied to the condition tests to prevent multiple event messages from being prepared and transmitted during the pendency of the condition. Further, pest sensor 46 input may be processed as needed to reduce the likelihood of an undesired outcome due to noise, activity of a nontargeted pest in the vicinity of the sensor, or slow, gradual changes with temperature. These type of adjustments may be particularly desirable for a flexible resistance-type sensor like that is associated with trap 90.

In one implementation directed specifically to a flex-varying electrical resistance rodent sensor as provided with trap 90, the rodent sensor signal value is exponentially smoothed using smoothing constants of $1/32$ and $31/32$ in accordance with equation (1) as follows:

$$\text{NewSmoothedValue} = ((1/32)*\text{NewSample}) + ((31/32)*\text{OldSmoothedValue}) \quad (1)$$

The operating logic computes the absolute value of the difference of the NewSample and OldSmoothedValue according to equation (2) as follows:

$$\text{DIFF} = \text{ABS}(\text{NewSample} - \text{OldSmoothedValue}) \quad (2)$$

DIFF is then compared against a programmable threshold value. If DIFF exceeds the threshold value, the sensor is determined to be "active" and a "hit" is registered by incrementing the value of a HIT COUNTER maintained by the operating logic. If DIFF does not exceed the threshold value, the HIT COUNTER is decremented until it reaches a terminal value of zero. Further, for this implementation, operating logic of controller 70 maintains a 6.4 second sliding time "aperture" over which the value of HIT COUNTER is examined. If HIT COUNTER exceeds a programmable threshold any time within this sliding 6.4 second interval, the operating logic interprets the condition as a rodent hit, and it prepares an event message for transmission indicating the active condition. By adjusting the programmable thresholds for DIFF and HIT COUNTER terminal values, this approach adjusts sensitivity of the rodent sensor, reducing false alarms and ensuring that true active conditions are detected and acted upon.

In addition to sensor signal processing, the 100 millisecond wake-up can also be used to scan for switch 76 activation and to provide for a blinking pattern of LED 82 and/or 84 as desired.

As previously indicated, this embodiment includes another wake-up mode for less frequently performed tasks. These tasks may include management of transceiver 52 and processing of inbound and outbound messages over the wireless communication path to gateway 33. Accordingly, controller 70 directs that receiver 56 listen for any possible transmissions from gateway 33 or other nodes 42 within communications range. Gateway 33, either directly or by routing its message through other nodes 42, may request status information of the subject node 42 by issuing a POLL REQUEST. If a valid POLL REQUEST is received, controller 70 prepares and sends a response packet including information about the operating status and sensor condition of the subject node 42 via transmitter 54. Such tasks further include a determination of whether the subject node 42 is being asked by a neighboring node 42 to relay a message according to routes established during installation of network 36. If such a request is made, controller 70 prepares and transmits the relay message via transceiver 52. In addition, on this less frequent basis, any event messages prepared during the more frequently performed tasks are sent via transmitter 54, and network maintenance/repair operations may be performed as further described hereinafter.

The operating logic of node 42 further includes a technique to re-form communications paths that become unreliable or unusable. To the extent needed, such self-healing may be performed on a less frequent basis (every second for example). Self-healing may occur due to the removal or failure of a relaying node 42 in an established path, or the introduction of an obstruction. In one implementation, node 42 determines the need to self-heal its communication path by maintaining a timer that is reset upon the receipt of a valid POLL REQUEST message from the corresponding gateway 33. The value of this timer is tested against a threshold value. If the timer reaches this threshold, the subject node 42 communication path is deemed to be lost, and a re-installation process is performed. This reinstallation is like that described in connection with procedure 220 of FIG. 4, starting with operation 224, except that operator activation of switch 76 is not necessary to perform path re-establishment, and reinstallation may be repeated a given number of times before declaring failure. In one example, the subject node 42 retries installation up to 3 more times at an interval equal to the programmable threshold value for the POLL REQUEST timer before declaring a failure.

For scheduled maintenance actions, an operator-activated switch can be used to cause the subject node 42 to prepare and transmit a message to gateway 33 indicating that it is being removed from service. In response, the gateway 33 removes the node's unique ID from its database of active nodes to halt subsequent polling. It should be appreciated that switch 76 could be used to signal removal if activated after successful addition to network 36 is indicated and/or by repeated actuation such that repeated actuation within a given time period toggles between a network install and node removal, or the like. Alternatively, a additional switch or other activation device may be utilized (not shown). Further, it should be appreciated that in other embodiments, node 42 may include more or fewer waking task modes with or without different frequencies, durations, or the like; may not have distinct sleep and wake modes, may alternatively or additionally be responsive to periodic or aperiodic polling inputs and/or interrupt type triggers to perform at least some tasks, and/or may perform more, fewer, or different tasks as required. Additionally or alternatively, network 36 may be at least partly predefined, rather than node-determined, may not include some or all of operator indicators, may not be self-healing, and/or may not provide for node removal.

In one alternative, certain nodes are transmit-only types that send sensor signals to other nodes capable of receiving and transmitting. Such other nodes may be dedicated communication routers with different sensing functionality than the transmit-only nodes (such as less/no sensing capability). For this alternative, these routers form a communication backbone between the remaining nodes and gateway 33.

Having described the operation of nodes 42 in greater detail, the complimentary operations of gateway 33 for each group 30 are next set forth. Gateway 33 serves as a data collector 32 in which status and event information from communicating nodes 42 is gathered. Gateway 33 communicates this information to centrally located data management server 120 hosting database 124. Server 120 provides for data visualization, analysis, reporting, and notification applications as further described in connection with FIG. 6. For the depicted embodiment, communications between gateway 33 and nodes 42 of a given group 30 take place via a wireless local area network 36, and between gateway 33 and server 120 via a wireless wide area network (WAN) using Internet Protocol (IP) over General Packet Radio Service (GPRS). Alternatively, hardwired telephone and/or fiber or coaxial cable connection could be used to interface gateway 33 to a computer network 24 connection with server 120, and/or other protocols and communication subsystems may be utilized.

Gateway communications may be of a routine, periodically scheduled type, or of an event/condition-driven type. Additionally, customer or administrator initiated queries or updates may be delivered to nodes 42. In one implementation, "downlink" communications from server 120 to gateway 33 utilize User Datagram Protocol (UDP), and "uplink" communications from gateway 33 to server 120, utilize File Transfer Protocol (FTP). Further, this nonlimiting implementation provides operating logic for gateway 33 as a collection of software tasks written in C# under the Microsoft Windows XP multithreading environment provided by Windows XP and the .NET Framework. A description of several exemplary tasks for this implementation are described as follows:

(a) Start-up: This task initializes communications peripherals including interface 250 and modem 260 to establish links to networks 36 and 25, respectively.

(b) Pairing Request Listener Task: Gateway 33 continuously monitors for messages over network 36 that indicate a new node 42 has joined the network 36 or has formed a new communications path to gateway 33. In one form, an SDP PAIRING REQUEST message is provided to gateway 33 upon successful completion of a new node 42 invocating a SEARCH REQUEST, which may occur when an installer activates the install mode with switch 76, or after a node 42 successfully self-heals a connection path to gateway 33. The SDP PAIRING REQUEST message contains information about the Node's identity, function (the node sensor type), and communications path, including QoS metrics. Gateway 33 checks the node identification (ID) against a locally stored list of currently installed nodes 42. If the node ID is new, the information, including communications path, is stored by gateway 33, and the newly added node 42 is added to the polling list of Nodes that should be polled during the Polling Task described hereinafter. If the Node ID is already in the database, only the updated path information is stored.

(c) Event Listener Task: Gateway 33 listens for unsolicited event messages from nodes 42 of its group 30, which are generated to indicate conditions, such as: Sensor Active, Low Battery, Sensor Fault, etc. Upon receipt of such an event message, gateway 33 attaches a local time stamp and forwards the event to server 120 over the GRPS connection using FTP.

(d) Polling Task: Gateway 33 implements a task to periodically poll each node 42 of its group 30 in a "round robin" fashion. Upon expiration of a configurable POLL TIMER, gateway 33 generates a POLL REQUEST for the next node 42 in succession from a listing of the installed nodes 42 and awaits a response. The resulting response message from the polled node 42 includes information such as sensor status, battery status, temperature, and condition, which is stored to a local database file and periodically sent to server 120 using FTP.

(e) Downlink Listener Task: Gateway 33 implements a task that continuously listens for "downlink" commands from server 120, which are received as User Datagram Protocol packets, and are used for remote configuration and diagnostics.

(f) Time Synchronization Task To maintain time accurate timing n between Server 120 and gateway 33, a Network Time Protocol is used to provide synchronization.

Figure 6:
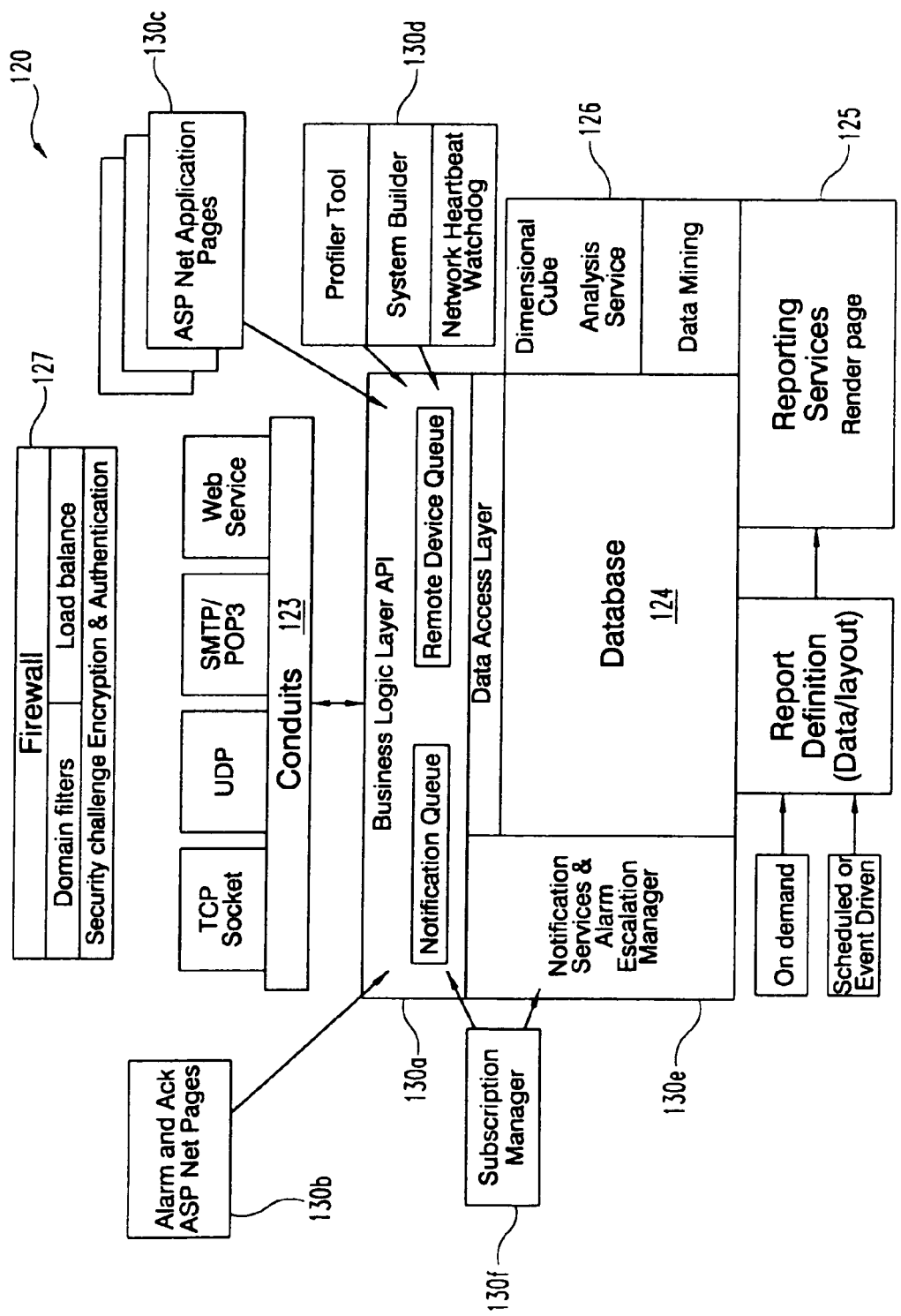
FIG. 6 is a diagrammatic view further depicting the data management server of the system of FIG. 1.

Referring to FIG. 6, the back-end data management server 120 is further depicted in diagrammatic form. Server 120 provides various virtual/logical components to allow sensor and node information from geographically disbursed gateways 33 to be aggregated into database 124. Server 120 has the ability to communicate with all remote pest control device groups 30, evaluate resulting data, and take corresponding actions using an Application Service Provider (ASP) model. Among other things, server 120 collects the information from the various sites (groups 30), aggregates and processes this information and determines what information needs to be forwarded to a customer. In addition, server 120 facilitates a data archive, notification and reporting process. Selected server functional components, as defined by software or other operating logic executed by server 120, are listed as follows:

(a) Firewall 127 provides customary data filtering, encryption, and authentication for communications over computer network 24.

(b) Conduits 123 define various application and transport communication protocols from gateways 33 or other information sources, such as UDP/IP (User Datagram Protocol), TCP/IP (Transmission Control Protocol), SMTP/POP3 (Email Based), or Web Service.

(c) Database 124 among other things, stores the sensor data collected in the field by groups 30. Additional stored data types are gateway 33, node 42, site, and user configuration and other external data feeds. This data provides business intelligence back to the user so sensor data can be interpreted as it relates to other environmental information i.e. air quality, temperature, rain amounts, etc. Applications 130 include a notifications and alarm service module 130e that can dispatch alerts to clients 122 (see FIG. 1) from database 124 based on subscriptions to the data and conditions set within the database 124. These subscriptions are managed by subscription manager module 130f. In one form, Microsoft SQL Server 2005 is the database engine for server 124. Reporting service module 125, analysis service module 126 (including data mining), various integration service modules are defined by this system. Server 120 defines a business logic layer Application Programming Interface (API) 130a including a notification queue managed by subscription manager module 130f and a remote device queue. Alarm and acknowledge ASP net pages 130b; ASP Net Application pages 130c; profiler, system builder, and network heartbeat watchdog modules 130d are also associated with this API.

(d) Web servers deliver applications 130 that allow users to interact with the data over the Word Wide Web using clients 122. In one form, the presentation layer application allowing graphical presentation of the data is written in ASP.NET.

Once an on-site technician installs all the nodes 42 for a given gateway 33, the site installation and configuration data is received by server 120 from the gateway 33. The data is then parsed at server 120 and stored in database 124. If a change to the configuration is necessary, the stored configuration data is modified and sent to the gateway 33. Gateway 33 will then retrieve this data and compare the modifications to implement any changes. Server 120 regularly receives event and sensor data from the gateway 33 of each group 30 and stores the values in the database. As new events take place at sensors 46, the corresponding data is sent to server 120 that performs notification services via module 120f to those recipients that have subscribed to the information. On a periodic basis (such as once a week), reports on trap activity and battery levels are also dispatched to recipients utilizing reporting services module 125.

Once sensor and node information is uploaded to server 120, it is available to the customer. Several methods are available for the customer to retrieve this information, depending on specified criteria, subscription level, and the nature of subsequent management action. Clients 122 (see FIG. 1) embody several customer interface options.

In one form, a password-protected web portal is provided to customers where they may log in to observe their corresponding sites/groups 30, generate reports with reporting services module 125, and observe the current status or summaries of recent events through a "dashboard" type of view. For those sensors 46 which by either its nature (say a moisture sensor) or customer interest (say a rodent station in food processing facility) require that event notification be nearly instantaneous, customers may choose to have notifications sent via e-mail, text message, fax or phone message (via clients 122c and/or 122d, for example). This alarm process can be managed interactively by responding to a server generated email or SMS communication, or by logging into the secure web portal. In contrast to such event-driven communications, for sensors where the information is more routine (say exterior rodent/termite bait stations), customers may choose to have summary reports delivered through spreadsheet reports or physical mailings on a scheduled basis. In one form, customer reports of site activity are customized to include customer-requested information on a requested schedule. Parameters governing how system 20 reacts to collected sensor information can be selected and set by the customers through a web interface. Such parameters include the time frame for notifications of a given sensor type, the delivery mechanism of any alerts, the scheduling of site status reports, etc. These may be updated and changed at any time by the customer. If an application is such that any action may be taken without direct human presence/intervention, such as flipping a switch, the system is capable of initiating such action as specified by customer need. For business systems that rely on the site data for billing and/or supervisory information, the data can be presented in a transport that allows integration into a customer business system.

Many further embodiments of the present application are envisioned. For example, one further embodiment includes: operating a pest control system including a plurality of pest control devices and a data collector, the pest control devices each including a respective pest attractant, a respective sensor, and a respective wireless communication circuit; wirelessly transmitting sensor information from the respective sensor of a first one of the pest control devices to a second one of the pest control devices; and wirelessly relaying the sensor information from the second one of the pest control devices to the data collector.

A further embodiment includes: a pest control system with a plurality of pest control devices and a data collector. The pest control devices each include a respective sensor and a respective wireless communication circuit. The system further includes means for wirelessly transmitting sensor information from the respective sensor of the first one of the pest control devices to a second one of the pest control devices, and means for wirelessly providing the sensor information from the second one of the pest control devices to the data collector.

Another embodiment comprises: providing a pest control system including a data collector and several pest control devices that each include a respective sensor and a respective wireless communication circuit; activating a network installation mode of operation of a selected one of the pest control devices; attempting to establish a wireless communication link with a pest control system communication network during the network installation mode, providing a first type of output to an operator if the wireless communication link is established; and providing a second type of output to the operator if the wireless communication link is not established.

Still another embodiment includes: a pest control system with a data collector and several pest control devices that each include a respective sensor and a respective wireless communication circuit. Also included are means for applying the magnetic field proximate to a selected one of the pest control devices, means for attempting to establish a wireless communication link with a pest control system communication network in response to the magnetic field, means for providing a first type of output to an operator if the wireless communication link is established, and means for providing a second type of output to the operator if the wireless communication link is not established.

Yet a further embodiment is directed to a pest control device that includes a pest sensor operable to provide one or more signals representative of pest detection and circuitry with a wireless communication transceiver coupled to the pest sensor to transmit information corresponding to the pest detection. This circuitry further includes a component responsive to a magnetic field proximate to the pest control device to operate the transceiver in an installation mode and a controller to execute operating logic to establish a wireless communication link with one or more devices during the installation mode. Also included is an indicator coupled to the circuitry to provide a first operator output indicative of establishment of the wireless communication link if the attempt succeeds and the second operator output indicative of failure to establish the wireless communication link.

A further embodiment includes: the first pest control device group including a plurality of wireless communication nodes that are each provided with a corresponding pest sensor and a first gateway to receive sensor data from the corresponding sensor of each of the wireless communication nodes. One or more of the wireless communication nodes includes the respective controller operating logic to define wireless communication network between the wireless communication nodes. The wireless communication network includes a first subset of the node to relay sensor information to the first gateway from a second subset of the node.

Any theory, mechanism of operation, proof, or finding stated herein is meant to further enhance understanding of the present application and is not intended to make the present application in any way dependent upon such theory, mechanism of operation, proof, or finding. It should be understood that any use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the invention has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A method, comprising:
   operating a pest control system including a plurality of pest control devices and a data collector, the pest control devices each including a respective pest sensor and a respective wireless communication circuit;
   wirelessly transmitting sensor information from the respective sensor of a first one of the pest control devices to a second one of the pest control devices;
   wirelessly providing the sensor information from the second one of the pest control devices to the data collector;
   activating an installation operational mode of the selected one of the pest control devices; and
   if the selected one of the pest control devices establishes a wireless communication link with any other of the pest control devices, providing output to an operator indicating establishment of the wireless communication link.

2. The method of claim 1, which includes applying a magnetic field proximate to a selected one of the pest control devices to initiate the activation of the installation operation mode, and wherein the selected one of the pest control devices includes a magnetic switch responsive to the magnetic field, the output includes a first visual indicator output, and further comprising:
   providing a second visual indicator output different than the first visual indicator output if the selected one of the pest control devices fails to establish the wireless communication link after a predefined period of time;
   in response to the second visual indicator output, installing one or more other of the pest control devices; and
   after the installing of the one or more other of the pest control devices, attempting again to establish the wireless communication link for the selected one of the pest control devices.

3. The method of claim 1, wherein the selected one of the pest control devices fails to establish the wireless communication link and further comprising:
   changing position of the selected one of the pest control devices; and
   establishing the wireless communication link with the selected one of the pest control devices after the changing of the position thereof.

4. A method, comprising:
   providing a pest control system including a data collector and several pest control devices, the pest control devices each including a respective sensor, and a respective wireless communication circuit;
   activating a network installation mode of a selected one of the pest control devices;
   during the network installation mode, attempting to establish a wireless communication link with a pest control system communication network;
   if the wireless communication link is established, providing a first type of output to an operator; and
   if the wireless communication link is not established, providing a second type of output to the operator.

5. The method of claim 4, which includes:
   wirelessly communicating information through the wireless communication link from the selected one of the pest control devices to the data collector by relaying the information with at least one other of the pest control devices; and
   in response to the second type of output to the operator, reattempting to establish the wireless communication link.

6. The method of claim 5, wherein the reattempting includes:
   increasing quantity of the pest control devices in the pest control communication network; and
   after increasing the quantity, reactivating the network installation mode of the selected one of the pest control devices to establish the wireless link with the pest system communication network.

7. The method of claim 5, wherein the reattempting includes:
changing relative position between the selected one of the pest control devices and at least one of: the data collector and any other of the pest control devices; and
after changing the relative position, reactivating the network installation mode of the selected one of the pest control devices to establish the wireless link with the pest system communication network.

8. The method of claim 4, which includes storing a first communication path including the communication link for the selected one of the pest control devices, the first communication path including a first one of the pest control devices to relay information to the data collector from the selected one of the pest control devices.

9. The method of claim 8, which includes:
detecting degradation of the first communication pathway;
replacing the first communication pathway with a second communication pathway for the selected one of the pest control devices, the second communication pathway including a second one of the pest control devices instead of the first one of the pest control device; and
storing the second communication path for the selected one of the pest control devices.

10. The method of claim 4, wherein the selected one of the pest control devices includes an operator activated switch, the first type of output includes a first illumination arrangement, and the second type of output includes a second illumination arrangement.

11. The method of claim 10, wherein the switch is of a magnetically responsive type, the activating of the network installation mode includes applying a magnetic field in proximity to the switch, and the first illumination arrangement includes a first visible light color and the second illumination arrangement includes a second visible light color different than the first visible light color.

12. The method of claim 4, wherein at least one of the pest control devices includes a respective bait to attract one or more species of pest.

13. An apparatus, comprising: a pest control device, including:
a pest sensor operable to provide one or more signals representative of pest detection;
circuitry including: a wireless communication transceiver coupled to the pest sensor to transmit information corresponding to the pest detection, a component responsive to a magnetic field proximate to the pest control device to operate the transceiver in an installation mode, and a controller to execute operating logic to establish a wireless communication link with one or more other devices during the installation mode; and
an indicator coupled to the circuitry to provide a first operator output indicative of establishment of the wireless communication link if the attempt succeeds, and a second operator output indicative of failure to establish the wireless communication link.

14. The apparatus of claim 13, wherein the pest control device includes a bait to attract one or more species of pest.

15. The apparatus of claim 14, further comprising a rodent trap and the pest sensor being structured to provide rodent trap status information.

16. The apparatus of claim 13, wherein the component includes at least one of a hall effect device and a magnetoresistor.

17. The apparatus of claim 13, further comprising a number of other pest control devices and a data collector in a communication gateway, the data collector including means for wirelessly communicating with the pest control device and the other pest control devices.

18. The apparatus of claim 17, further comprising:
a computer network in communication with the gateway; and
a data management server in communication with the computer network.

19. The apparatus of claim 18, wherein:
the gateway includes means for communicating sensor status information from the pest control device to the data management server; and
the data management server includes:
means for storing and evaluating the sensor status information;
means for accessing data stored with the data management server by a user over the computer network.

20. The apparatus of claim 13, wherein the circuitry includes a processing device and logic executable by the processing device to determine and store information representative of a wireless communication pathway through the one or more other devices.

21. The apparatus of claim 13, further comprising:
a number of gateways each in wireless communication with a respective one of a number of different pest control device groups, the pest control device belonging to one of the groups, the gateways each gathering data from the respective one of the different pest control device groups;
a computer network in communication with the gateways; and
a data management server in communication with the computer network, that includes means for storing and evaluating pest control device information from each of the different pest control device groups, means for accessing data stored with the data management server by one or more users over the computer network.

22. The apparatus of claim 20, wherein the logic executed by the processing device includes means for providing adjustable sensitivity of the pest sensor.

* * * * *